United States Patent

Inamoto et al.

[11] 4,002,690
[45] Jan. 11, 1977

[54] 4-HOMOISOTWIST-3-YL-CARBINOL

[75] Inventors: Yoshiaki Inamoto; Hiroshi Ikeda; Naotake Takaishi, all of Wakayama; Kiyoshi Tsuchihashi, Kainan, all of Japan

[73] Assignee: Kao Soap Co., Ltd., Tokyo, Japan

[22] Filed: July 14, 1975

[21] Appl. No.: 595,557

[30] Foreign Application Priority Data

July 16, 1974    Japan .............................. 49-81534

[52] U.S. Cl. .................... 260/617 F; 260/514 G; 424/343
[51] Int. Cl.² ......................................... C07C 35/22
[58] Field of Search ................ 260/617 F; 424/343

[56] References Cited

UNITED STATES PATENTS 3,907,908    9/1975    Light et al. .................... 260/617 F

OTHER PUBLICATIONS

Krantz et al., Chem. Comm., p. 1287 (1971).
Mirrington et al., J. Org. Chem., vol. 37, pp. 2871–2881, (1972).
Fieser & Fieser, Reagents for Org. Lymthins, pp. 584–586, (1967).

*Primary Examiner*—Bernard Helfin
*Assistant Examiner*—James H. Reamer
*Attorney, Agent, or Firm*—Woodhams, Blanchard and Flynn

[57] ABSTRACT

4-homoisotwist-3-yl-carbinol having the formula (II):

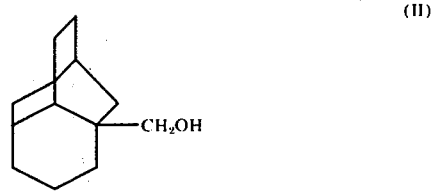

(II)

is prepared by reducing 4-homoisotwistane-3-carboxylic acid or a salt or lower alkyl ester thereof, having the formula (I):

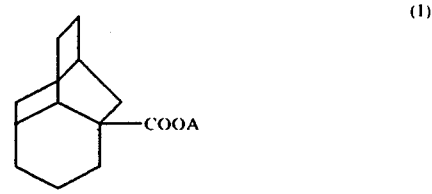

(I)

wherein A is hydrogen, one equivalent of an alkali metal or an alkaline earth metal, or an alkyl group having 1 to 8 carbon atoms.

1 Claim, No Drawings

4-HOMOISOTWIST-3-YL-CARBINOL

BACKGROUND OF THE INVENTION

1. Field of the Invention

This invention relates to the compound, 4-homoisotwist-3-yl-carbinol (II) (tricyclo[5.3.1.0$^{3,8}$]undec-3-yl-carbinol), and a process for preparing same. More particularly, this invention relates to 4-homoisotwist-3-yl-carbinol (II) which is prepared by reducing 4-homoisotwistane-3-carboxylic acid or a salt or lower alkyl ester thereof (I) as shown by the following reaction equation:

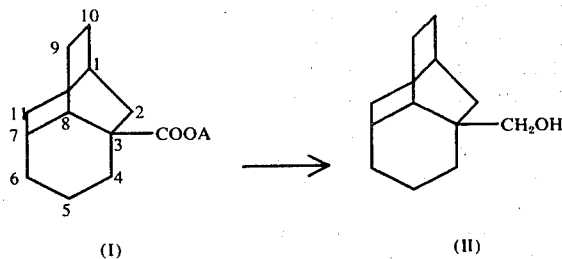

wherein A is hydrogen, one equivalent of an alkali metal or an alkaline earth metal, or an alkyl group having 1 to 8 carbon atoms.

2. Description of the Prior Art 4-homoisotwistane is a novel tricyclic basket-type hydrocarbon which was recently discovered (Krantz et al, Chem. Commun., 1287 (1971); Majerski et al., Tetrahedron Lett., 4915 (1973); Schleyer et al., Chemistry Lett., 1189 (1973); and the inventors of this application, Chemistry Lett., 1185 (1973)). The properties and activities of this compound are not fully known, but it is known that it can be transformed to 1-methyladamantane, a known useful compound as described in U.S. Ser. Nos. 485,068 and 485,069, both filed July 2, 1974. No derivatives of this compound have previously been synthesized.

SUMMARY OF THE INVENTION

We have discovered 4-homoisotwist-3-yl-carbinol (II). This compound has biological activity as an antiviral agent, a modifier moiety for various pharmaceutical compounds and a plant hormone. This compound also is useful as an additive for lubricating oils, a high pressure lubricant, a rust-preventive agent and a compound of an oiling agent composition for fibers in the same way as known adamantane compounds. Further, the compound is an intermediate valuable for synthesis of various useful substances. See the section entitled "Adamantane"in the Supplement Volume of Kirk-Othmer's "Encyclopedia of Chemical Technology".

The compound of this invention can be obtained by reducing 4-homoisotwistane-carboxylic acid or a salt or lower alkyl ester thereof represented by the formula (I). Various known reactions are applicable to the performance of this reduction. For example, a reduction of the carboxylic acid (I) (A=H) or its salt (A= metal) or its lower alkyl ester (A=lower alkyl) with a complex metal hydride such as lithium aluminum hydride and sodium borohydride, reduction of the lower alkyl ester with a metal (or a metal hydride) and an alcohol (Bouveault-Blanc reaction), and catalytic hydrogenation reduction using, for example, an Adkins (copper-chromium) catalyst, are effectively employed in this invention.

4-homoisotwistane-3-carboxylic acid (A is hydrogen in the formula (I)), which is one of starting substances that can be used in this invention, is synthesized by a process developed by us, as described Japanese patent application Ser. No. 81535/74, filed July 16, 1974 (corresponding to U.S. application Ser. No. 595,556 filed July 14, 1975, entitled "4-Homoisotwistane-3-Carboxylic Acid and Process for Preparing Same", the entire contents of which are incorporated herein by reference. More specifically, this compound can be synthesized by reacting 4-homoisotwistane with t-butyl alcohol and formic acid in the presence of sulfuric acid as a catalyst according to the Koch carboxylation reaction. This carboxylic acid (I) is a novel compound, and its salts and lower alkyl esters are also novel compounds that can easily be derived from this carboxylic acid by known methods.

The fact that in the 4-homoisotwistyl-carbinol compound obtained by the process of this invention, the hydroxymethyl group is present at the 3-position of 4-homoisotwistane is proved by the following matters.

As pointed out hereinabove, the carboxylic acid (A is hydrogen in the formula (I)), that is the starting substance for preparing the carbinol according to this invention, is prepared by the Koch reaction of 4-homoisotwistane. It is known that in the Koch reaction, the reactivity of tertiary carbon atoms (bridgehead carbons in the case of 4-homoisotwistane) is much higher than that of secondary or primary carbon atoms. In view of the foregoing, it is conjectured that in 4-homoisotwistane-carboxylic acid, the carboxyl group can be introduced into the 1-position, 3-position (equivalent to the 7-position) or 8-position, and that there is no possibility that the carboxyl group will be introduced into a position other than the above three positions. This conjecture is supported by the nmr of this carboxylic acid.

Namely, in the nmr spectrum of this carboxylic acid, only one acidic proton, namely the proton of the carboxylic acid, that disappears on treatment with heavy water, appears isoltatedly in a lower magnetic field. If it is supposed that the carboxyl group is introduced at a position other than a bridgehead position, namely the position of a secondary carbon atom, only one proton attached to the secondary carbon atom should be isolated from the remaining protons by the influence of the carboxyl group and it should appear on the side of a lower magnetic field. However, in the actual nmr spectrum, only a complex multiplet is observed in the region of δ 2.6– 0.8.

In view of the foregoing, it is concluded that in 4-homoisotwistane-carboxylic acid, the carboxyl group is introduced into the 1-position, 3-position (equivalent to the 7-position) or 8-position, and that there is no possibility that the carboxyl group will be introduced into a position other than the above three positions. When the proton nmr of the present carbinol (II) is measured in the presence of tris(dipivaroylmethanate) europium (Eu (dpm)$_3$) while varying the concentration thereof, there is observed the presence of two protons and a hydroxy proton attached to the carbinol carbon, 5 different protons which shift greatly toward the side of a low magnetic field with an increase of the concentration of Eu(dpm)$_3$ and 2 different protons which are on the side of a high magnetic field and hardly shift (in addition, there are 10 different protons which are situated between the two groups of protons and these have not been sufficiently analyzed). Among the possible carbinols derived from the three possible kinds of 4-homoisotwistane-carboxylic acids having the carboxyl group at the 1-, 3- or 8-position, only the 3-substituted carbinol would exhibit the above behavior to such a shift reagent. According to the empirical law that the size of the low magnetic field shift of a proton by Eu(dpm)$_3$ is in inverse proportion to the square or cube of the distance between said proton and the Eu atom in the Eu(dpm)$_3$-carbinol complex (Cockerill et al, Tetrahedron Lett., 5145, 5143 (1970) and C. C. Hinckley J. Amer. Chem. Soc., 91, 5160 (1969)), in the molecular model of Dreiding, the distances of the protons from the Eu atom (it is supposed that the Eu atom is located on an extension of the line connecting the C$_3$ atom of the skeleton to the carbinol carbon, based on the teaching of Cockerill et al, Chem. Rev., 73, 553 (1973)) are estimated. Thus, it is seen that only 5 protons are relatively close to the Eu atom and they are different from one another (it is considered that they correspond to $H_s^9$, $H_x^2$, $H^8$, $H_a^4$ and $H_e^4$ in the formula (IIa) given below, respectively); and that only two protons are scarcely influenced by the Eu atom and they are different from each other (corresponding to $H_x^{11}$ and $H_e^6$). Only the 3-carbinol compound (II) satisfies the above conditions. Incidentally, since both the 1-carbinol and 8-carbinol compound has in the molecule a symmetric face (passing through C$_1$-C$_{10}$-C$_9$-C$_8$-C$_5$), if there were present protons close to the Eu atom, the number of such protons should naturally be an even number.

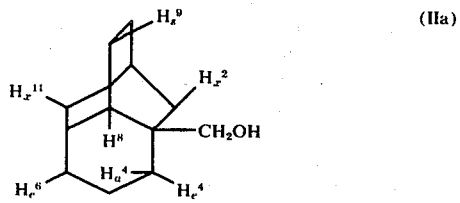

(IIa)

Also in view of the reactivity of bridgehead carbon atoms (Schleyer et al, J. Amer. Chem. Soc., 93, 3189 (1971)), it can be assured that the 3-carboxylic acid (I) is formed by the Koch reaction of 4-homoisotwistane. If viewed from a different point, the 3-position of 4-homoisotwistane is the bridgehead 1-position of bicyclo [3.3.1]nonane in which an ethano bridge is laid between the 3- and 9-positions (see the formula (III) given below). Further, if viewed from a still different point, the 1- and 8-positions of 4-homoisotwistane correspond to the bridgehead 4- and 1-positions of bicyclo[2.2.2]octane in which a trimethylene bridge is laid between the 2- and 6-positions (see the formula (IV) given below). If the influences caused by the ethano and trimethylene bridges are neglected, the reactivity of the 1-position in the formula (III) is 10$^4$ times as high as the reactivity of the 1- or 4-position in the formula (IV).

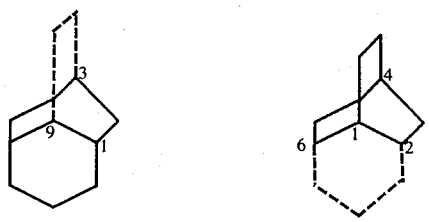

(III)            (IV)

In the synthesis of 4-homoisotwistane-3-carboxylic acid (I) used as the starting substance of this invention according to the above-mentioned Koch reaction, there is no possibility of the occurrence of isomerization of the skeleton of 4-homoisotwistane.

When 4-homoisotwistane is reacted with t-butyl alcohol alone in the presence of sulfuric acid without addition of formic acid, 4-homoisotwistane is not changed at all and it is recovered almost quantitatively. Accordingly, it is proven that under the conditions of the Koch reaction the skeleton of 4-homoisotwistane (I) is not changed, and it remains as it was at the start.

This invention will now be further described in detail by reference to the following illustrative Examples.

Preparation 1

Synthesis of 4-homoisotwistane-3-carboxylic acid (A is hydrogen in formula (I)).

A mixture of 15 g (0.10 mole) of 4-homoisotwistane, 100 ml of cyclohexane and 450 g of 95% of sulfuric acid was cooled by ice water to maintain the mixture at 10° – 15° C., and a solution of 30 g (0.41 mole) of t-butyl alcohol in 55 g (1.20 moles) of 99% formic acid was added dropwise to the above mixture over a period of 2.5 hours, with agitation. After completion of the dropwise addition, the mixture was further agitated for 3 hours at the same temperature.

The reaction mixture was placed in 1 Kg of ice pieces, and after the organic layer was separated, the water layer was extracted with cyclohexane and the extract was combined with the organic layer. The resulting mixture was washed with water and extracted 3 times with a 1.5% solution of sodium hydroxide.

To the sodium hydroxide extract was added dropwise 35% hydrochloric acid to adjust the pH to 1–2, and the mixture was extracted with diethyl ether. The ether extract was dried with anhydrous sodium sulfate and was fractionated. A fraction boiling at 135° – 140° C. under 0.9 mm Hg was collected to give 12.5 g (yield = 63%) of crude 4-homoisotwistane-3-carboxylic acid (A is H in the formula (I)).

When the product was allowed to stand still, it solidified to form white crystals. The crystals were sublimed under reduced pressure to give a pure product having a melting point of 95° – 85° C.

Elemental Analysis Values for C$_{12}$H$_{18}$O$_2$: Found: C = 75.0%, H = 9.5%; Calculated: C = 74.19%, H = 9.34%; ir (neat, cm$^{-1}$): 2940, 2920, 2860 1680, 1470, 1460, 1450, 1400, 1285, 1275, 1260; nmr (CDCl$_3$, TMS internal standard, δ): 2.6 – 0.8 (complex multiplet, 17H); 10.20 (singlet, 1H, disappearing on D$_2$O treatment) MS (m/e) (relative intensity, %): 194 (M$^+$, 12), 150 (13), 149 (100), 92 (12), 80 (19), 78 (15), 66 (27), 57 (12), 41 (17).

Preparation 2

Synthesis of methyl 4-homoisotwistane-3-carboxylate (A is CH$_3$ in the formula (I)):

A mixture of 12 g (0.062 mole) of 4-homoisotwistane-3-carboxylic acid obtained in Preparation 1 and 30 g of thionyl chloride was heated and refluxed on an oil both for 1 hour. The majority of the excess thionyl chloride was distilled off under atmospheric pressure and 20 ml of benzene was added the residue. An azeotropic benzene-thionyl chloride mixture was distilled off under reduced pressure. This distillation of thionyl chloride with benzene was repeated 3 times. The residue was cooled and agitated, and 40 ml of methanol was added dropwise to the residue over a period of about 15 minutes. After completion of the dropwise addition, the reaction was carried out at room temperature for 30 minutes and then under reflux for 1 hour.

The reaction mixture was allowed to cool to ambient temperature and was placed in 500 ml of ice water, and the mixture was extracted with benzene and the benzene extract was washed with water, a saturated aqueous solution of sodium hydrogencarbonate and water, and then dried with anhydrous sodium sulfate.

The majority of the benzene was distilled off from the resulting benzene solution under atmospheric pressure and the residue was fractionated under reduced pressure. A fraction boiling at 86° – 88° C. under 0.9 mm Hg was collected to give 7.8 g (yield = 61%) of methyl 4-homoisotwistane-3-carboxylate. $n_D^{23.5}$: 1.4887

Elemental Analysis Values for $C_{13}H_{20}O_2$: Found: C = 74.5%, H = 9.9% Calculated: C = 74.96%, H = 9.68% ir (neat, cm$^{-1}$): 2950, 2920, 2860, 1730, 1460, 1450, 1430, 1270, 1250, 1230, 1210, 1190, 1170, 1160, 110, 1080; nmr $CCDCl_3$, TMS internal standard, $\delta$): 2.6 – 0.8 (complex, multiplet, 17 H) 3.64 (singlet, 3H); ms (m/e) (relative intensity, %): 208 (10, M$^+$), 150 (13), 149 (100), 107 (7), 93 (9), 91 (6), 79 (10), 81 (14), 67 (21), 41 (7).

EXAMPLE 1

Synthesis of 4-homoisotwist-3-yl-carbinol (II):

1.6 g (0.042 mole) of lithium aluminum hydrive was dispersed in 100 ml of dry diethyl ether, and a solution of 7.5 g (0.036 mole) of methyl 4-homoisotwistane-3-carboxylate obtained in Preparation 2 in 20 ml of dry diethyl ether was added dropwise to the above dispersion at such a rate that a gradual reflux state was attained. About 30 minutes was required for completion of the dropwise addition. After completion of the dropwise addition, the mixture was refluxed under agitation for 1.5 hours, and the mixture was then allowed to cool to room temperature. Then, 10 ml of methyl alcohol was added to the mixture to separate unreacted lithium aluminum hydride.

The reaction mixture was placed in 500 ml of ice water and extracted with diethyl ether, and the ether extract was washed with water and dried with anhydrous sodium sulfate. The ether solution was fractionated and a fraction boiling at 96° – 98° C. under 0.6 mm Hg was collected to give 3.3 g (yield = 51%) of 4-homoadamant-3-yl-carbinol (II).

Melting Point: 107° – 108° C.

Elemental Analysis Values for $C_{12}H_{20}O$: Found: C = 80.1%, H = 11.3%; Calculated: C = 79.94%, H = 11.18%; ir (neat, cm$^{-1}$): 3640, 3300, 2900, 1460, 1030, 1120, 800; nmr (CDCl$_3$, TMS internal standard, $\delta$): 3.25 (multiplet, 2H); 2.20 (singlet, 1H); 2.3 – 017 (complex multiplet, 17 H); ms (m/e) (relative intensity, %): 180 (3,M$^+$), 150 (14), 149 (100), 93 (11), 81 (19), 79 (13), 67 (29), 41 (11).

EXAMPLE 2

The anti-viral activity of 4-homoisotwist-3-yl-carbinol (II) prepared in Example 1 was tested against Newcastle disease virus (NDV) in an in vitro test using chick embryo monolayer tissue culture as follows.

A chick embryo monolayer tissue culture was mixed with NDV solution having a concentration of 128 hemagglutinin aggregation units and with an aqueous suspension of the carbinol (II) in the culture, and then cultured at 37° C for 48 hours. The concentration of the replicated virus in the resulting tissue culture was determined by a hemagglutination reaction.

| Concentration in the Starting Tissue Culture ($\mu$g/ml) | % Inhibition of NDV Multiplications* | |
|---|---|---|
| | II | Amantadine.HCl |
| 156 | 99.8 | 0.0 |
| 78 | 91.2 | 0.0 |
| 39 | 0.0 | 0.0 |

*Relative to the control experiment in which no II or Amantadine. HCl was added.

Thus the virus replication in the tissue culture containing above 39$\mu$g/ml of carbinol (II) was almost completely inhibited. This result apparently shows that the antiviral activity of the carbinol (II) is extremely superior to that of Amantadine hydrochloride which is an established antiviral agent for men and domestic animals.

The carbinol (II) also has a potent antiviral activity in vivo. The method of administration and dosage to be employed in the use of the compound (II) are similar to those conventionally used for representative antiviral agents, and the details can readily be discerned and determined by those who are familiar with the arts in the field.

The embodiments of the invention in which an exclusive property or privilege is claimed are defined as follows:

1. 4-Homoisotwist-3-yl-carbinol.

* * * * *